US008409207B2

(12) United States Patent  
Lyons

(10) Patent No.: US 8,409,207 B2  
(45) Date of Patent: Apr. 2, 2013

(54) OSTEOCHONDRAL AUTOGRAFT TRANSPLANTATION PROCEDURE AND APPARATUS

(75) Inventor: Christopher Michael Lyons, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 403 days.

(21) Appl. No.: 12/892,220

(22) Filed: Sep. 28, 2010

(65) Prior Publication Data

US 2011/0015633 A1    Jan. 20, 2011

Related U.S. Application Data

(62) Division of application No. 11/735,348, filed on Apr. 13, 2007, now Pat. No. 7,875,032.

(51) Int. Cl.  
*A61B 17/56* (2006.01)

(52) U.S. Cl. .......... 606/79; 606/86 R; 606/184

(58) Field of Classification Search ...... 30/113.1–113.3, 30/114–117, 179; 83/743–745; 408/97, 408/115 R, 115 B, 241 G; 433/41, 43, 72, 433/74–76; 606/79–80, 83–84, 86 R, 87–88, 606/96–97, 167–189; 623/23.63, 908, 919  
See application file for complete search history.

(56) References Cited

U.S. PATENT DOCUMENTS

| | | | |
|---|---|---|---|
| 4,306,866 | A | 12/1981 | Weissman |
| 4,538,946 | A | 9/1985 | Bloch |
| 4,759,666 | A | 7/1988 | Grab |
| 5,645,549 | A | 7/1997 | Boyd et al. |
| 5,919,196 | A | 7/1999 | Bobic et al. |
| 5,921,987 | A | 7/1999 | Stone |
| 5,954,671 | A | 9/1999 | O'Neill |
| 6,007,496 | A | 12/1999 | Brannon |
| 6,110,209 | A | 8/2000 | Stone |
| 6,395,011 | B1 | 5/2002 | Johanson et al. |
| 6,488,033 | B1 | 12/2002 | Cerundolo |
| 6,767,354 | B2 | 7/2004 | Johanson et al. |
| 7,001,393 | B2 | 2/2006 | Schwenke et al. |
| 7,160,305 | B2 | 1/2007 | Schmieding |
| 7,182,766 | B1 | 2/2007 | Mogul |
| 7,264,634 | B2 | 9/2007 | Schmieding |
| 7,747,306 | B2 | 6/2010 | Nycz et al. |
| 2004/0034437 | A1 | 2/2004 | Schmieding |
| 2004/0039400 | A1 | 2/2004 | Schmieding et al. |
| 2004/0193154 | A1 | 9/2004 | Leatherbury et al. |
| 2005/0222687 | A1 | 10/2005 | Vunjak-Novakovic et al. |
| 2006/0060209 | A1 | 3/2006 | Shepard |
| 2007/0019852 | A1 | 1/2007 | Schildkraut et al. |
| 2007/0149982 | A1 | 6/2007 | Lyons |
| 2007/0172506 | A1 | 7/2007 | Nycz et al. |
| 2007/0233264 | A1 | 10/2007 | Nycz et al. |
| 2008/0051677 | A1 | 2/2008 | Bharadwaj |

Primary Examiner — Kevin T Truong  
Assistant Examiner — Larry E Waggle, Jr.

(57) ABSTRACT

A surgical procedure according to which a cutting device is connected in a spaced relationship to an anchor, and the anchor is located over a first area of the bone. The distance between the cutting device and the anchor is adjusted so that the cutting device extends over a second area of the bone, and the anchor is driven into the first area of the bone so that the cutting device cuts into the second area.

5 Claims, 2 Drawing Sheets

OSTEOCHONDRAL AUTOGRAFT TRANSPLANTATION PROCEDURE AND APPARATUS

BACKGROUND

This invention relates to an improved osteochondral autograft transplantation procedure and apparatus, and more particularly, to such a procedure and apparatus in which a graft is implanted in a recipient opening.

The human knee consists of three bones—a femur, a tibia, and a patella—that are held in place by various ligaments. The corresponding condyles of the femur and the tibia form a hinge joint, and the patella protects the joint. Portions of the condyles, as well as the underside of the patella, are covered with an articular cartilage, which allow the femur and the tibia to smoothly glide against each other without causing damage.

The articular cartilage often tears, usually due to traumatic injury or degenerative processes. This tearing does not heal well due to the lack of nerves, blood vessels and lymphatic systems; and the resultant knee pain, swelling, and limited motion of the bone(s) must be addressed.

Damaged adult cartilages have historically been treated by a variety of surgical interventions including lavage, arthroscopic debridement, and repair stimulation, all of which provide less than optimum results.

Another known treatment involves removal and replacement of the damaged cartilage with a prosthetic device. However, prostheses have largely been unsuccessful since they are deficient in the elastic, and therefore in the shock-absorbing, properties characteristic of the cartilage. Moreover, prostheses have not proven able to withstand the forces inherent to routine knee joint function.

In an attempt to overcome the problems associated with the above techniques, osteochondral autograft transplantation, also known as "mosaicplasty" has been used to repair articular cartilages. This procedure involves removing injured tissue from the damaged area and drilling one or more openings in the underlying bone. A graft, or plug, consisting of healthy cartilage overlying bone, is obtained from another area of the patient, typically from a lower weight-bearing region of the joint under repair, or from a donor patient, and is implanted in each opening. Although it is extremely important that each plug fit in its opening in a precise manner, this is difficult since it is often impossible to cut a graft the same size as the diameter of the defect. Although a series of grafts having a circular cross section could be cut and then placed in the defect, this would not be practical since voids or spaces would be present between the adjacent grafts.

Therefore, what is needed is a technique in which a series of grafts can be harvested and placed in a closely-spaced relationship in the defect with a minimum of spacing between the grafts. The present invention relates to such a technique.

DETAILED DESCRIPTION

Figure 1:
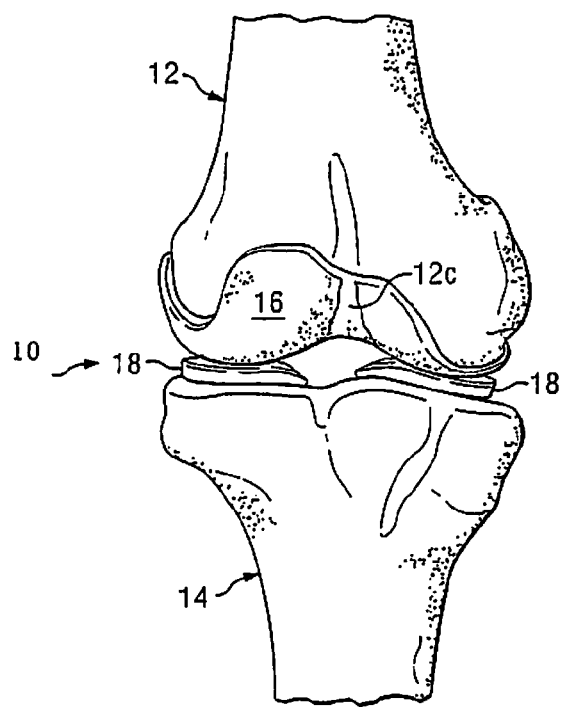
FIG. 1 is an elevational view of a human knee with certain parts removed in the interest of clarity.

Referring to FIG. 1 of the drawing, the reference numeral 10 refers, in general, to a knee area of a human including a femur 12 and a tibia 14 whose respective condyles are in close proximity. A cartilage 16 extends over a portion of the condyle of the femur 12, and a meniscus 18 extends between the cartilage and the tibia 14. The patella, as well as the tendons, ligaments, and quadriceps that also form part of the knee, are not shown in the interest of clarity.

Figure 2:
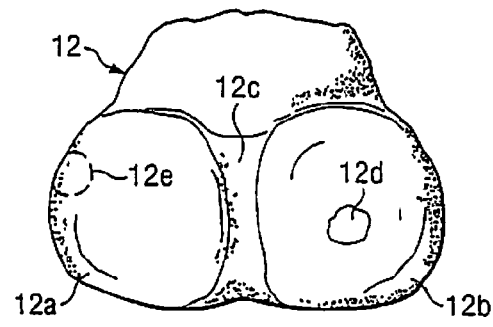
FIG. 2 is an elevational view of the femur of the knee of FIG. 1 rotated ninety degrees from its position in FIG. 1.

FIG. 2 depicts the femur 12 of FIG. 1 rotated ninety degrees to better show its lateral condyle 12a, its medial condyle 12b, and its intercondylar notch 12c that extends between the condyles 12a and 12b. It will be assumed that a portion of the cartilage 16 extending over the medial condyle 12b been damaged or has worn away, leaving a damaged area, or defect 12d.

Figure 3:
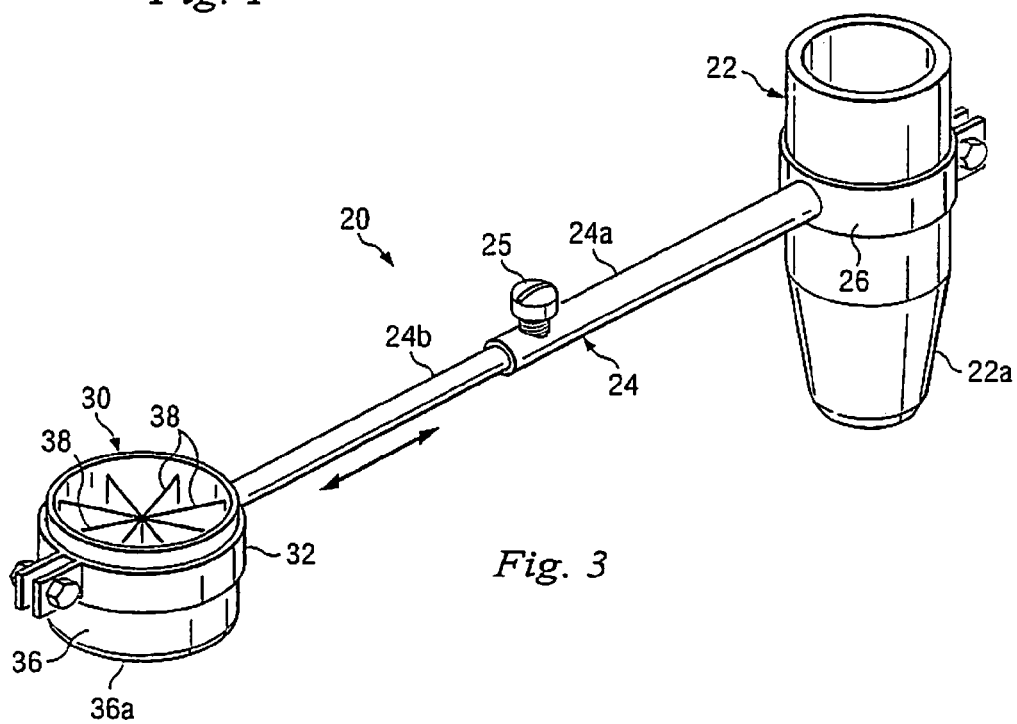
FIG. 3 is an isometric view of an embodiment of an apparatus used in the procedure of the present invention.

Referring to FIG. 3, an apparatus 20 is provided which includes a solid cylindrical anchor 22 connected to one end of an arm 24 by a connecting strap 26 that is adjustable so as to vary the tightness on the anchor. One end portion 22a of the anchor 22 (the lower end portion as viewed in FIG. 3) is tapered radially inwardly, for reasons to be described.

The arm 24 consists of two telescoping sections 24a and 24b with the section 24a having a slightly larger diameter than the section 24b. An end portion of the section 24b extends in the corresponding end portion of the section 24a and can be secured therein in any conventional manner, such as by a threaded bolt 25 that extends through a threaded opening in the section 24a and engages a portion of the section 24b. Thus, the length of the end portion of the section 24b that is received by, or telescoped into, the end portion of the section 24a is variable so as to vary the length of the arm 24.

Figure 4:
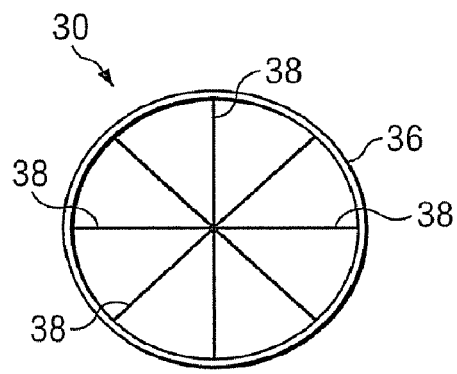
FIG. 4 is an enlarged bottom plan view of a component of the apparatus of FIG. 3.

The other end of the arm section 24b is connected to a cutting device 30 by a connecting strap 32 that is adjustable so as to vary the tightness on the device 30. The device 30 consists of a hollow, open-ended, cylindrical housing 36 having a circular cutting edge 36a formed at its lower end. As shown in FIG. 4, eight angularly-spaced cutting blades 38 (FIG. 4) are mounted in the housing 36 in any conventional manner. Each cutting blade 38 extends from the center of the housing 36 to the interior wall of the housing, and the blades are spaced at approximately forty-five degrees intervals.

Referring to FIG. 2, it will be assumed that it is desired to harvest a graft, or grafts, from an undamaged, non-loadbearing area of the femur 12, such as an area 12e in the lateral condyle 12a, and to implant the graft or grafts in the defect 12d. To this end, an opening, or void, must be formed in the bone of the femur 12 below the defect 12d to receive a graft. Thus, the arm 24 is connected between the anchor 22 and the cutting device 30 and its length is adjusted in the manner described above in accordance with the following procedure.

Figure 5:
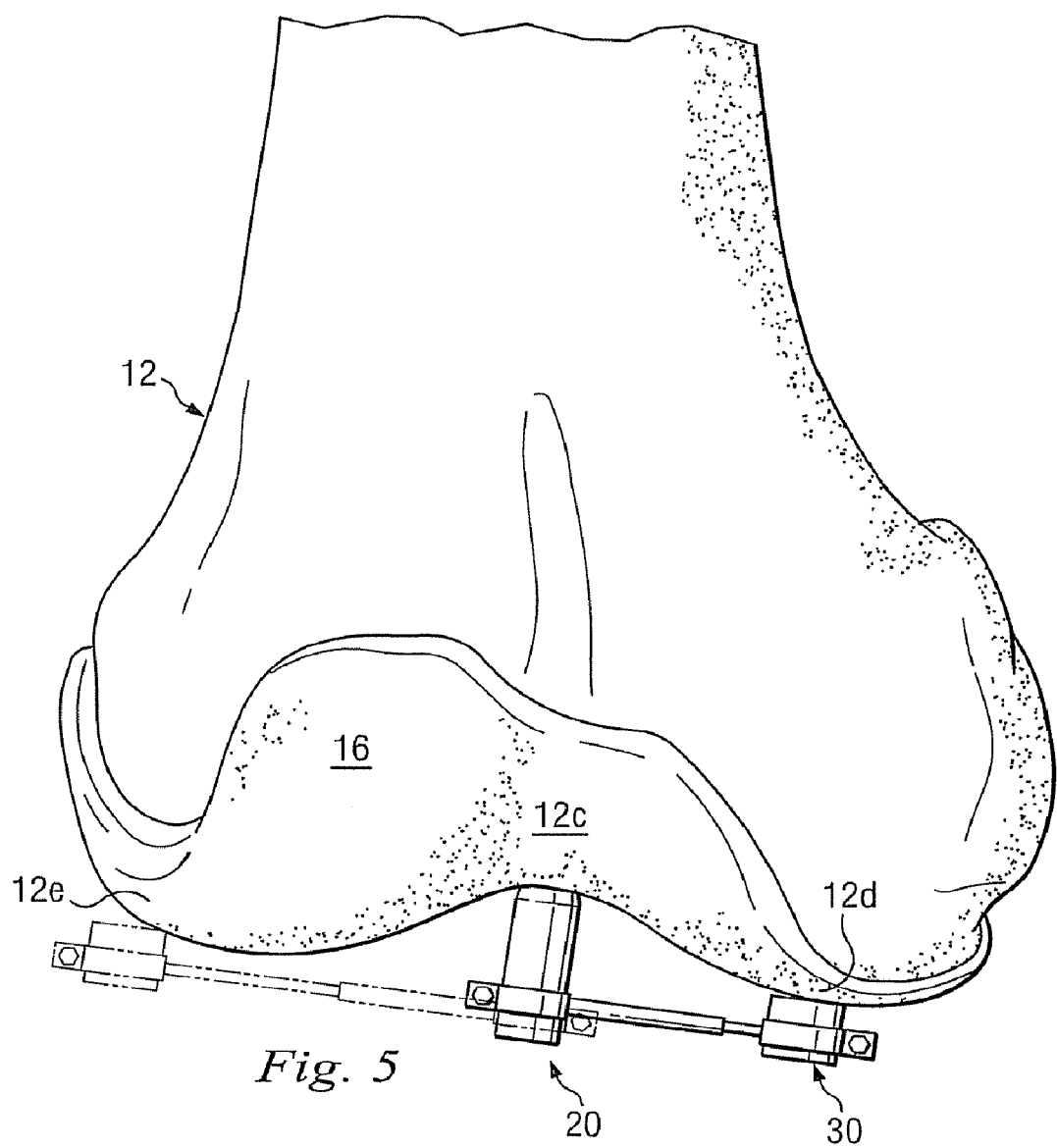
FIG. 5 is an enlarged view of the femur portion of the knee depicted in FIG. 1, and depicting the apparatus of FIG. 3.

The apparatus 20 is positioned relative to the femur 12 in the position by the solid lines in FIG. 5, i.e. with the anchor 22 extending over a portion of the notch 12c of the femur. The length of the arm 24 is adjusted so that the cutting device 30 extends over the defect 12d. The distances that the portions of the anchor 22 and the housing 36 extend from the straps 26 and 32, respectively, and towards the femur 12 are adjusted in accordance with the depth of the cut that is desired in accordance with the following.

The anchor 22 is driven into the bone of the femur 12 using a hammer or the like, to anchor it in the femur. This movement of the anchor 22 is transferred to the device 30 by the arm 24 and the driving of the anchor continues until the cutting edge 36a of the housing 36 of the device 30 engages the outer surface of the cartilage 16 surrounding the defect 12d. Alternately, the anchor 22 can be driven into the bone of the femur until it is stable, without regard to the position of the device 30. Then the strap 26 can be loosened and the arm 24 adjusted relative to the anchor 22 until the edge 36a engages the outer surface of the cartilage 16, after which the strap is tightened around the anchor.

In either case, the anchor 22 is then driven further into the bone in the notch 12c a distance corresponding to the desired depth of the opening of the defect 12d, which movement is transferred to the device 30 so that it cuts an opening in the bottom wall of the defect to this depth. The cutting is done by the edge 36a of the housing 36 and the blades 38, resulting in a circular cut formed by eight pie-shaped sections. The depth of this cut can be gauged by the surgeon by observing indicia on the anchor 22 and/or the housing 36, or by observing the position of the band 26 or the arm 24 relative to the surface of the cartilage 16.

The surgeon then manipulates the housing 36 as needed to remove the cut sections of the underlying bone in the defect 12d, and the cut sections are discarded.

The strap 26 is then loosened and raised on the anchor 22 to raise the arm 24 and the device 30. The device 30 is then swung about the anchor 22 to a position shown by the phantom lines in FIG. 5 in which it extends over the area 12e with the length of the arm 24 being adjusted accordingly. The strap 32 is tightened and the anchor 22 is driven further into the femur 12 and this movement of the anchor 22 is transferred to the device 30 by the arm 24. The device 30 thus cuts through the cartilage 16 and the bone of the femur 12 at the area 12e. The depth of this cut can be gauged by the surgeon by observing indicia on the anchor 22 and/or the housing 36, or by observing the position of the band 26 or the arm 24 relative to the surface of the cartilage 16 so that the depth is the same as the depth of the cut in the defect 12d.

The graft can then be implanted into the opening in the defect 12d using one of two techniques. According to one technique, the strap 26 is loosened on the anchor 22 and the device 30, with the graft sections embedded therein, is then swung back to the defect 12d. The height of the strap 26 on the anchor is adjusted so that the device 30 extends just above the upper surface of the defect 12d. The graft sections can then be tapped from the housing 36 into the defect 12d including the opening formed below the defect.

The other implantation technique can be a technique disclosed in one or more of assignee's U.S. patent application Ser. No. 10/792,780, filed on Mar. 5, 2004 (now U.S. publication no. 2004/0176771, published Sep. 9, 2004); U.S. patent application Ser. No. 10/785,388, filed on Feb. 23, 2004 (now U.S. application publication no. 2004/0193154, published Sep. 30, 2004); U.S. patent application Ser. No. 10/984,497, filed Nov. 9, 2004; (now U.S. application publication no. 2005/0101962, published May 12, 2005); U.S. patent application Ser. No. 10/815,778, filed Apr. 2, 2004 (now U.S. application publication no. 2005/0222687, published Oct. 6, 2005); U.S. patent application Ser. No. 08/885,752, filed Jun. 30, 1997 (now U.S. Pat. No. 5,919,196 granted Jul. 6, 1999); U.S. patent application Ser. No. 08/797,973, filed Feb. 12, 1997 (now U.S. Pat. No. 5,921,987 granted Jul. 13, 1999); U.S. patent application Ser. No. 08/908,685, filed Aug. 7, 1997 (now U.S. Pat. No. 5,964,805, granted Oct. 12, 1999); U.S. patent application Ser. No. 08/774,799 filed Dec. 30, 1996 (now U.S. Pat. No. 6,007,496); U.S. patent application Ser. No. 09/187,283, filed on Nov. 5, 1998 (now U.S. Pat. No. 6,110,209, granted Aug. 29, 2000); U.S. patent application Ser. No. 09/425,337, filed Oct. 22, 1999 (now U.S. Pat. No. 6,306,142, granted Oct. 23, 2001); U.S. patent application Ser. No. 09/559,532, filed Apr. 28, 2000 (now U.S. Pat. No. 6,375,658, granted Apr. 23, 2002); U.S. patent application Ser. No. 09/118,680, filed Jul. 17, 1998 (now U.S. Pat. No. 6,395,011, granted May 28, 2002); U.S. patent application Ser. No. 09/624,689, filed Jul. 24, 2000 (now U.S. Pat. No. 6,440,141, granted Aug. 27, 2002); U.S. patent application Ser. No. 09/571,363, filed May 15, 2000 (now U.S. Pat. No. 6,488,033, granted Dec. 3, 2002); U.S. patent application Ser. No. 09/243,880, filed Feb. 3, 1999 (now U.S. Pat. No. 6,592,588, granted Jul. 15, 2003); U.S. patent application Ser. No. 10/004,388, filed Oct. 23, 2001 (now U.S. Pat. No. 6,767,354, granted Jul. 27, 2004); U.S. patent application Ser. No. 10/084,490, filed Feb. 28, 2002 (now U.S. Pat. No. 6,852,114, granted Feb. 8, 2005); U.S. patent application Ser. No. 10/665,152, filed on Sep. 22, 2003 (now U.S. publication no. 2004/0059425, published Mar. 25, 2004); U.S. patent application Ser. No. 10/638,489, filed on Aug. 12, 2003 (now U.S. publication no. 2004/0034437, published Feb. 19, 2004); U.S. patent application Ser. No. 10/443,893, filed on May 23, 2003 (now U.S. publication no. 2004/0039400, published Feb. 26, 2004); U.S. patent application Ser. No. 10/947,217, filed on Sep. 23, 2004 (now U.S. publication no. 2006/0060209, published Mar. 23, 2006); U.S. patent application Ser. No. 11/339,194 filed Jan. 25, 2006; U.S. patent application Ser. No. 11/317,985 filed Dec. 23, 2005; U.S. patent application Ser. No. 11/340,884 filed Jan. 27, 2006; U.S. patent application Ser. No. 11/514,433 filed Sep. 1, 2006; and U.S. patent application Ser. No. 11/508,349 filed Aug. 23, 2006. The disclosures of each of these patent applications, publications, and patents are incorporated herein by reference.

Thus, according to the procedure of the present invention, the depth of the graft is identical to that of the opening in the defect 12d thus assuring that the cartilage portion of the graft will align with the cartilage 16 surrounding the defect.

It is understood that variations can be made in the above, including the following:

(1) The present invention procedure is not limited to preparing a graft for implantation in the knee, but is equally applicable to other parts of the body.

(2) The surgeon can be provided with a plurality of cutting devices that are similar to the cutting device 30, but having different diameters, and the surgeon can select the one most compatible in size with the defect 12d.

(3) The anchor 22 and the cutting device 30 can be used in areas of the knee that are different from those discussed above.

(4) Rather than cut the opening in the defect 12d with the cutting device 30, it can be cut independently by the surgeon prior to the anchoring of the anchor 22 in the notch 12c.

(5) More than one opening, of the type described above, can be formed at or near the defect and a graft can be implanted in each opening.

(6) A mechanism other than the rings 26 and 32 can be used to connect the arm 24 to the anchor 22 and the device 30.

(7) The graft could take the form of a synthetic or natural material/scaffold used for resurfacing the defect.

(8) The number of blades on the cutting device 30, and therefore the number of graft segments that are cut, can vary.

Those skilled in the art will readily appreciate that many other variations and modifications of each embodiment described above can be made without materially departing from the novel teachings and advantages of this invention. Accordingly, all such variations and modifications are intended to be included within the scope of this invention as defined in the following claims. In the claims, means-plus-function clauses are intended to cover the structures described herein as performing the recited function and not only structural equivalents, but also equivalent structures.

What is claimed is:

1. Apparatus for harvesting a graft for implantation in an opening in a bone of a human body, the apparatus comprising:
   an anchor;
   a cutting device;
   a telescoping arm connecting the anchor and the cutting device;
wherein the arm comprises a first section and a second section, the first section configured to have a diameter larger than a diameter of the second section, with the second section configured to telescopically slide within the first section and the arm being adapted to permit rotation of the cutting device relative to the anchor, wherein the anchor has a tapered portion adapted to be driven into the bone, wherein the driving of the anchor into one area of the bone causes the cutting device to cut into another area of the bone.

2. The apparatus of claim 1 wherein the cutting device comprises a cylindrical housing having a plurality of blades adapted to make a circular cut into the bones to form a graft.

3. The apparatus of claim 2 wherein a cutting edge is formed on the housing to cut a circular graft and wherein the blades cut the graft into a plurality of sections.

4. The apparatus of claim 1 wherein the cutting device is rotatable relative to the anchor to cut an opening in the bone and harvest a graft for implantation into the opening.

5. The apparatus of claim 4 wherein the cutting device is adapted to transfer the graft to the opening.

* * * * *